(12) United States Patent
Jones et al.

(10) Patent No.: US 8,591,473 B2
(45) Date of Patent: Nov. 26, 2013

(54) MANUALLY RETRACTED SAFETY NEEDLE WITH RIGID WING STRUCTURE

(75) Inventors: Scott Jones, University City, MO (US); George Clark, Lewis Center, OH (US)

(73) Assignee: Covidien LP, Mansfield, MA (US)

(*) Notice: Subject to any disclaimer, the term of this patent is extended or adjusted under 35 U.S.C. 154(b) by 1314 days.

(21) Appl. No.: 11/525,623

(22) Filed: Sep. 22, 2006

(65) Prior Publication Data
US 2007/0088262 A1    Apr. 19, 2007

Related U.S. Application Data

(60) Provisional application No. 60/719,763, filed on Sep. 22, 2005.

(51) Int. Cl.
- *A61M 5/32* (2006.01)
- *A61M 5/00* (2006.01)
- *A61B 5/00* (2006.01)

(52) U.S. Cl.
USPC ............ 604/198; 604/110; 604/177; 600/576

(58) Field of Classification Search
USPC .............. 604/110, 162, 164.08, 165.03, 177, 604/192, 197, 198, 263; 600/576
See application file for complete search history.

(56) References Cited

U.S. PATENT DOCUMENTS

| | | | |
|---|---|---|---|
| 4,170,993 A * | 10/1979 | Alvarez | 604/180 |
| 4,183,246 A | 1/1980 | Reynolds | |
| 4,326,519 A * | 4/1982 | D'Alo et al. | 604/165.04 |
| 4,445,893 A * | 5/1984 | Bodicky | 604/165.04 |
| 4,676,783 A | 6/1987 | Jagger et al. | |
| 4,690,675 A | 9/1987 | Katz | |
| 4,711,636 A * | 12/1987 | Bierman | 604/180 |
| 4,747,831 A | 5/1988 | Kulli | |
| 4,781,692 A | 11/1988 | Jagger et al. | |
| 4,813,426 A | 3/1989 | Haber et al. | |
| 4,820,282 A | 4/1989 | Hogan | |

(Continued)

FOREIGN PATENT DOCUMENTS

| | | |
|---|---|---|
| EP | 0 566 769 A1 | 10/1993 |
| EP | 1 221 300 A2 | 7/2002 |

(Continued)

OTHER PUBLICATIONS

International Search Report (Form PCT/ISA/210 (first & second sheet) (Apr. 2005) for International Appln. No. PCT/US06/37278, filed Sep. 22, 2006.

(Continued)

*Primary Examiner* — Kevin C Sirmons
*Assistant Examiner* — William Carpenter
(74) *Attorney, Agent, or Firm* — Lisa E. Winsor, Esq.

(57) ABSTRACT

A manually retracted safety needle device is provided having a rigid wing structure to stabilize the safety needle against the body of a patient. The safety needle device includes an elongate housing having a hub movably mounted therein. A tissue penetrating needle extends distally from the hub and a fluid conveying tube extends proximally from the hub. The rigid wing structure extends substantially along the length of the elongate member and, in one embodiment, includes wings extending transversely to a longitudinal axis of the elongate member. The safety needle is also provided with various finger gripping structures to facilitate manipulation of the safety needle device relative to the patient.

22 Claims, 12 Drawing Sheets

(56) References Cited

U.S. PATENT DOCUMENTS

| | | | | |
|---|---|---|---|---|
| 4,850,961 A | * | 7/1989 | Wanderer et al. | 604/508 |
| 4,863,432 A | * | 9/1989 | Kvalo | 604/177 |
| 4,900,307 A | | 2/1990 | Kulli | |
| 4,900,311 A | | 2/1990 | Stern et al. | |
| 4,973,316 A | | 11/1990 | Dysarz | |
| 4,994,034 A | | 2/1991 | Botich et al. | |
| 5,084,030 A | | 1/1992 | Byrne et al. | |
| 5,085,639 A | | 2/1992 | Ryan | |
| 5,088,982 A | | 2/1992 | Ryan | |
| 5,102,394 A | * | 4/1992 | Lasaitis et al. | 604/164.08 |
| 5,108,376 A | | 4/1992 | Bonaldo | |
| 5,114,410 A | | 5/1992 | Caralt Batlle | |
| 5,120,320 A | * | 6/1992 | Fayngold | 604/177 |
| 5,125,414 A | | 6/1992 | Dysarz | |
| 5,129,884 A | | 7/1992 | Dysarz | |
| 5,147,327 A | | 9/1992 | Johnson | |
| 5,176,655 A | | 1/1993 | McCormick et al. | |
| 5,188,119 A | | 2/1993 | Sunderland | |
| 5,188,599 A | | 2/1993 | Botich et al. | |
| 5,192,275 A | * | 3/1993 | Burns | 604/263 |
| 5,226,894 A | | 7/1993 | Haber et al. | |
| 5,232,456 A | | 8/1993 | Gonzalez | |
| 5,267,961 A | | 12/1993 | Shaw | |
| 5,273,540 A | | 12/1993 | Luther et al. | |
| 5,312,359 A | * | 5/1994 | Wallace | 604/164.08 |
| 5,318,538 A | | 6/1994 | Martin | |
| 5,330,438 A | | 7/1994 | Gollobin et al. | |
| 5,338,303 A | | 8/1994 | King et al. | |
| 5,376,075 A | | 12/1994 | Haughton et al. | |
| 5,385,551 A | | 1/1995 | Shaw | |
| 5,389,076 A | | 2/1995 | Shaw | |
| 5,395,347 A | | 3/1995 | Blecher et al. | |
| 5,407,431 A | | 4/1995 | Botich et al. | |
| 5,409,461 A | | 4/1995 | Steinman | |
| 5,423,758 A | | 6/1995 | Shaw | |
| 5,498,241 A | | 3/1996 | Fabozzi | |
| 5,501,675 A | | 3/1996 | Erskine | |
| 5,538,508 A | | 7/1996 | Steyn | |
| 5,549,571 A | | 8/1996 | Sak | |
| 5,554,130 A | | 9/1996 | McDonald et al. | |
| 5,562,629 A | | 10/1996 | Haughton et al. | |
| 5,562,634 A | | 10/1996 | Flumene et al. | |
| 5,573,510 A | | 11/1996 | Isaacson | |
| 5,575,777 A | | 11/1996 | Cover et al. | |
| 5,578,011 A | | 11/1996 | Shaw | |
| 5,591,138 A | | 1/1997 | Vaillancourt | |
| 5,632,733 A | | 5/1997 | Shaw | |
| 5,676,658 A | | 10/1997 | Erskine | |
| 5,695,475 A | | 12/1997 | Best, Jr. et al. | |
| 5,746,215 A | | 5/1998 | Manjarrez | |
| 5,779,679 A | * | 7/1998 | Shaw | 604/158 |
| 5,810,775 A | | 9/1998 | Shaw | |
| 5,928,199 A | | 7/1999 | Nakagami | |
| 5,931,815 A | | 8/1999 | Liu | |
| 5,951,525 A | | 9/1999 | Thorne et al. | |
| 5,954,708 A | * | 9/1999 | Lopez et al. | 604/533 |
| 5,997,512 A | | 12/1999 | Shaw | |
| 6,015,438 A | | 1/2000 | Shaw | |
| 6,056,726 A | | 5/2000 | Isaacson | |
| 6,080,137 A | | 6/2000 | Pike | |
| 6,090,078 A | | 7/2000 | Erskine | |
| 6,096,005 A | | 8/2000 | Botich et al. | |
| 6,179,812 B1 | | 1/2001 | Botich et al. | |
| 6,210,371 B1 | | 4/2001 | Shaw | |
| 6,221,055 B1 | | 4/2001 | Shaw et al. | |
| RE37,439 E | | 11/2001 | Firth et al. | |
| 6,494,863 B1 | | 12/2002 | Shaw et al. | |
| 6,517,522 B1 | | 2/2003 | Bell et al. | |
| 6,524,276 B1 | | 2/2003 | Halseth et al. | |
| 6,547,762 B1 | | 4/2003 | Botich et al. | |
| 6,572,584 B1 | | 6/2003 | Shaw et al. | |
| 6,582,402 B1 | | 6/2003 | Erskine | |
| 6,620,136 B1 | | 9/2003 | Pressly, Sr. et al. | |
| 6,641,555 B1 | | 11/2003 | Botich et al. | |
| 6,659,984 B2 | | 12/2003 | Maclean et al. | |
| 6,673,047 B2 | | 1/2004 | Crawford et al. | |
| 6,743,186 B2 | | 6/2004 | Crawford et al. | |
| 6,773,419 B2 | | 8/2004 | Crawford et al. | |
| 6,786,875 B2 | | 9/2004 | Barker et al. | |
| 6,835,190 B2 | | 12/2004 | Nguyen | |
| 6,860,872 B2 | | 3/2005 | Teichert | |
| 6,905,478 B2 | | 6/2005 | Ingram et al. | |
| 6,945,960 B2 | | 9/2005 | Barker et al. | |
| 6,969,376 B2 | * | 11/2005 | Takagi et al. | 604/263 |
| 6,972,002 B2 | | 12/2005 | Thorne | |
| 6,976,976 B2 | | 12/2005 | Doyle | |
| 7,037,292 B2 | | 5/2006 | Carlyon et al. | |
| 2002/0099340 A1 | * | 7/2002 | Crawford et al. | 604/263 |
| 2002/0103465 A1 | * | 8/2002 | Crowford et al. | 604/263 |
| 2003/0040717 A1 | | 2/2003 | Saulenas et al. | |
| 2003/0078540 A1 | | 4/2003 | Saulenas et al. | |
| 2003/0083624 A1 | * | 5/2003 | Smith et al. | 604/177 |
| 2003/0093035 A1 | * | 5/2003 | Mohammed | 604/195 |
| 2003/0176842 A1 | | 9/2003 | Wilkinson et al. | |
| 2003/0199830 A1 | | 10/2003 | Nguyen | |
| 2003/0220619 A1 | | 11/2003 | Polidoro et al. | |
| 2004/0143195 A1 | | 7/2004 | Bressler et al. | |
| 2004/0193110 A1 | | 9/2004 | Giambattista et al. | |
| 2004/0267200 A1 | | 12/2004 | Carlyon et al. | |

FOREIGN PATENT DOCUMENTS

| EP | 1 221 305 B1 | 10/2005 |
|---|---|---|
| JP | 04-180772 | 6/1992 |
| JP | 2002-011098 | 1/2002 |
| JP | 2002-210018 | 7/2002 |
| JP | 2002-210018 A | 7/2002 |
| WO | WO 00/47256 | 8/2000 |

OTHER PUBLICATIONS

Office Action issued Jun. 11, 2012 from related Japanese Patent Application Serial No. 2008-532433, 1 pg.

Office Action issued Aug. 16, 2012 from European Application No. 06804065.8, 5 pages.

European Search Report dated Jul. 20, 2012 from European Application No. 06804065.8, 3 pages.

English translation of Notice of Reasons for Rejection from corresponding Japanese Application No. 2011-286268 issued Feb. 18, 2013, 2 pages.

English Translation of Decision on Dismissal of Amendment issued Mar. 29, 2013 in related Japanese Patent Application No. 2008-532433, 2 pgs.

* cited by examiner

MANUALLY RETRACTED SAFETY NEEDLE WITH RIGID WING STRUCTURE

CROSS REFERENCE TO RELATED APPLICATION

This patent application claims priority to U.S. Provisional Application Ser. No. 60/719,763, filed Sep. 22, 2005, which is incorporated herein in its entirety by reference.

BACKGROUND

1. Technical Field

The present disclosure relates to the field of medical needle assemblies for the administration and withdrawal of fluids to and from the body. More particularly, the present disclosure relates to safety needle assemblies having rigid wing structure to facilitate stabilization of the needle assemblies relative to the patient.

2. Background of Related Art

Hypodermic needles are used for venous access in a variety of medical procedures requiring fluid sampling, percutaneous medication injection, or other delivery to or withdrawal of fluid from a patient. Various intravenous needle assemblies are known which can generally include blood collection needles, infusion needles, hemodialysis needles, needles associated with blood collection bags, etc. Problems associated with the use of intravenous needle assemblies may include needlestick injury, stabilization of the needle relative to the patient, and ease of insertion and withdrawal of the needle from the patient.

Some of the health risks associated with hazardous needle exposure include HIV, hepatitis, and other blood-borne pathogens. Medical professionals are in danger of contracting such blood-borne pathogens from infected patients by inadvertent needle sticks from a contaminated needle employed during medical, dental, laboratory, etc. procedures.

Certain known intravenous assemblies, such as, for example, winged intravenous assemblies, are employed whereby a patient receives intravenous delivery of a fluid or a fluid collection procedure is performed. A needle is connected through a winged body of the assembly to an intravenous tube. The wings are typically flexible and are used to manipulate the assembly during insertion and withdrawal of the needle from the patient. Specifically, the wings are typically folded up and pinched between the thumb and forefinger of the user during insertion of the needle into the patient. The wings are also used to stabilize the assembly against the patient, and provide a surface area for taping, attachment, etc. to the patient to prevent movement of the assembly in relation to the patient. The winged intravenous assembly must be similarly manipulated to withdraw the assembly from the patient and dispose of it without creating a risk of needlestick injury to the medical personnel.

While the known intravenous needle assemblies typically employ flexible wings to assist in insertion and stabilization of the needle assembly relative to the patient, the dual nature of the flexible wings may not optimize the ability to safely insert the needle into the patient and securely stabilize the intravenous assembly relative to the patient once it has been inserted.

Therefore, it would be desirable to have an intravenous needle assembly having a dedicated rigid wing structure for stabilizing the needle assembly relative to the patient. It would additionally be desirable to have dedicated structure on the intravenous needle assembly to facilitate grasping by the user and aid in insertion and withdrawal of the needle from the patient. Additionally, it would be desirable to have an intravenous needle assembly whereby the needle itself maintains a relatively low-profile relative to the stabilizing wing and skin surface of the patient. Furthermore, it would be desirable to have a safety needle assembly which maintains the needle in an extended position until released by the operator and which retains the needle in a locked proximal position, contained within an associated housing, to prevent reuse and/or needlestick injury.

SUMMARY

The presently disclosed safety needle generally includes an elongate housing and a hub movably mounted within the elongate housing. A hollow needle extends distally from the hub while a fluid tube extends proximally from the hub. The disclosed safety needle includes a rigid wing extending longitudinally along the outer surface of the elongate housing and a dorsal fin. In one embodiment, the rigid wing includes a pair of side wings extending transverse to a longitudinal axis of the elongate housing in a first direction and the dorsal fin extends from the hub along an axis transverse to a longitudinal axis of the hub in a second direction. The dorsal fin facilitates insertion of the hollow needle into a patient and is movable longitudinally within a longitudinal slot formed in the elongate housing.

The safety needle further includes a release mechanism associated with the hub and the elongate housing. In one embodiment, the release mechanism includes a notch positioned distally of longitudinal slot and a flexible finger provided on the hub and movable into and out of the notch to secure and release the hub relative to the elongate housing. In one embodiment, the flexible finger is provided with a finger pad to facilitate movement of the flexible finger into and out of the notch.

In one embodiment, the safety needle includes lockout structure to secure the hub in a proximal most position with the needle contained within the elongate housing. The lockout structure includes at least one projection extending into a space defined by the slot at a location adjacent the proximal end of the slot. The hub includes a projection movable within the slot, for example the flexible finger, which can be retracted proximally beyond the projection and is retained within a proximal most position within the slot by the projection.

There is also disclosed a safety needle device having an elongate housing and a hub movably mounted within the elongate housing. A needle extends distally of the hub. In this embodiment, a finger gripping surface is provided on a proximal end of the elongate housing to facilitate insertion of the needle within the patient. The elongate housing is provided with a longitudinally extending slot and, in one embodiment, a first portion and a second portion of the finger gripping surfaces are provided on opposed sides of the slot. The finger gripping surfaces are ribbed to provide secure control of the elongate housing by the fingers of the user. The finger gripping surfaces extend around a portion of the periphery of the proximal end of the elongate number.

In one embodiment, the disclosed safety needle includes an elongate housing and a hub movably mounted within the elongate housing. A needle extends distally from the hub and a rigid wing is provided on an outer surface of the elongate housing. A finger gripping surface is provided on a proximal end of the elongate housing to facilitate manipulation of the safety needle. The housing has and a longitudinally extending slot and a portion of the finger gripping surface is provided on either side of the longitudinally extending slot. In one embodiment, the finger gripping surfaces are ribbed.

In a particular embodiment, the rigid wing extends longitudinally along an outer surface of the elongate member. In another embodiment, the rigid wing extends transversely to the longitudinal axis of the elongate member. In this embodiment, the rigid wing includes a pair of generally rectangular wings extending transversely to a longitudinal axis of the elongate member.

In the disclosed embodiments, at least a portion of the hub is transparent to view the flow of fluids therethrough.

DESCRIPTION OF THE DRAWINGS

Various embodiments of the presently disclosed safety needle are disclosed herein with reference to the drawings, wherein.

DETAILED DESCRIPTION OF EMBODIMENTS

Embodiments of the presently disclosed manually retracted safety needle device having a rigid wing structure will now be described in detail with reference to the drawings wherein like numerals designate identical or corresponding elements in each of the several views. As is common in the art, the term 'proximal' refers to a position or location on a device closer to the user or operator, i.e. surgeon or physician, while the term "distal" refers to a position or location on a device further away from the user.

Figure 1:
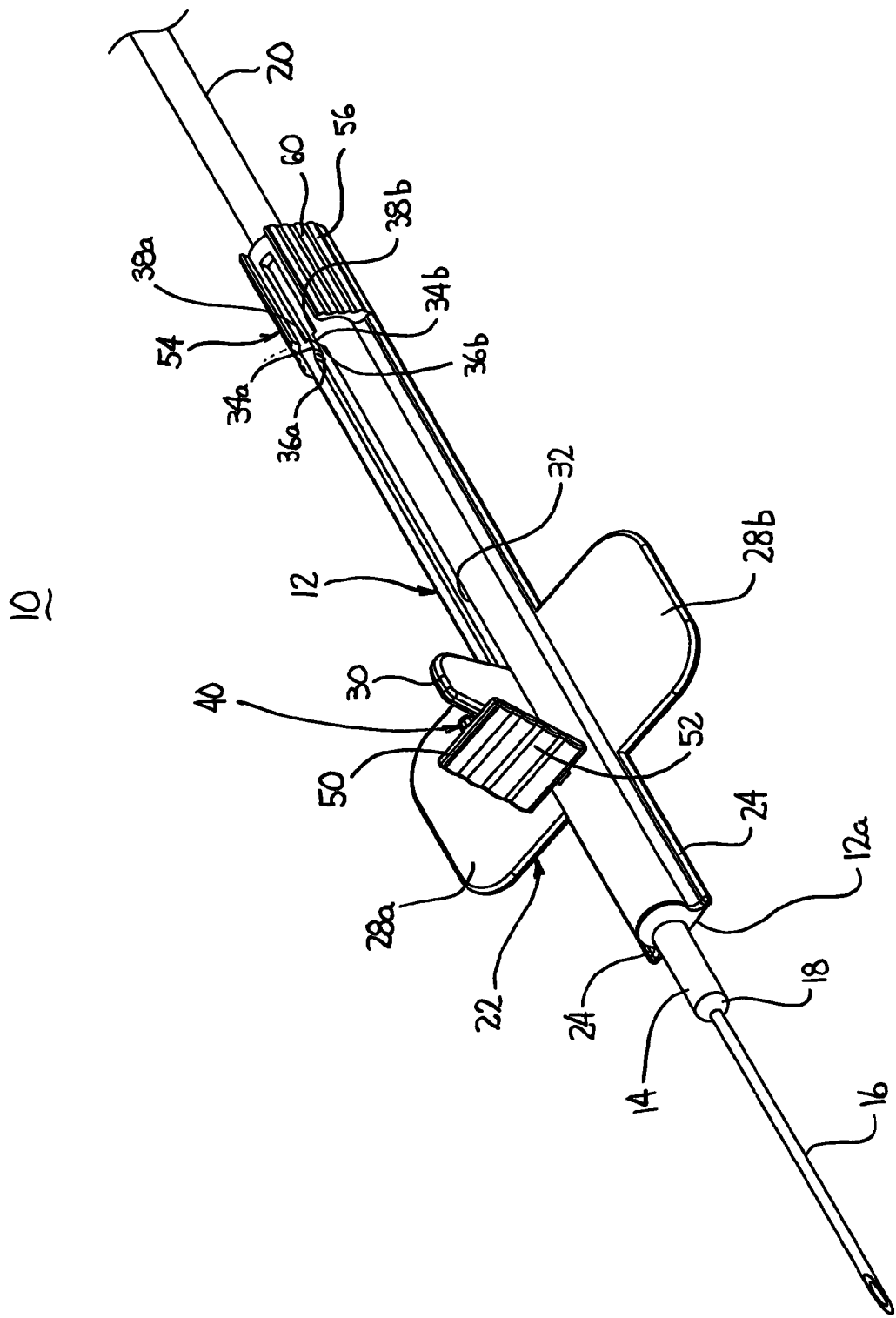
FIG. 1 is a perspective view of one embodiment of a manually retracted safety needle device having a rigid wing structure.

FIG. 1 illustrates one embodiment of the presently disclosed manually retracted rigid wing safety needle 10 suitable for use in a variety of surgical procedures where fluids are to be injected or withdrawn from the body of a patient. Safety needle 10 generally includes an elongate housing 12 having a hub 14 movably mounted within elongate housing 12. In one embodiment, the bottom of elongate housing 12 defines a flat surface 12a for supporting safety needle 10 on the body of a patient. A hollow needle 16 extends from a distal end 18 of hub 14. A hollow tubing 20 extends from elongate housing 12 and is in fluid communication with hub 14 and needle 16. Safety needle 12 includes a rigid wing structure 22 which is provided to stabilize safety needle 10 on the arm of a patient. Unlike prior art safety needles, which generally have flexible wing structures to facilitate insertion of the needle into the arm of the patient and to stabilize the needle on the arm of a patient by taping or otherwise affixing the flexible wings to the arm of the patient, the provision of rigid wing structure 22 on safety needle 10 reduces the likelihood that safety needle 10 will flex or wobble on the arm of the patient. In one embodiment, housing 12 includes side extensions 24 which extend outwardly from flat surface 12a. Side extensions 24 improve the stability of safety needle 10 and extend along all or a portion of the length of elongate housing 12.

Rigid wing structure 22 includes at least one rigid wing which extends perpendicularly to a longitudinal axis of elongate housing 12. As shown in FIG. 1, a pair of rigid wings 28a and 28b can be provided. Each rigid wing 28a and 28b is generally rectangular and extends transversely from elongate housing 12. Each of rigid wings 28a and 28b can be formed integrally with or attached to housing 12. Rigid wings 28a and 28b stabilizes safety needle 10 on the arm of a patient, e.g., prevents twisting of safety needle 10, and provides additional location points for securing the safety needle 10 to the arm of the patient through various known methods such as, for example, taping, etc.

Figure 4:
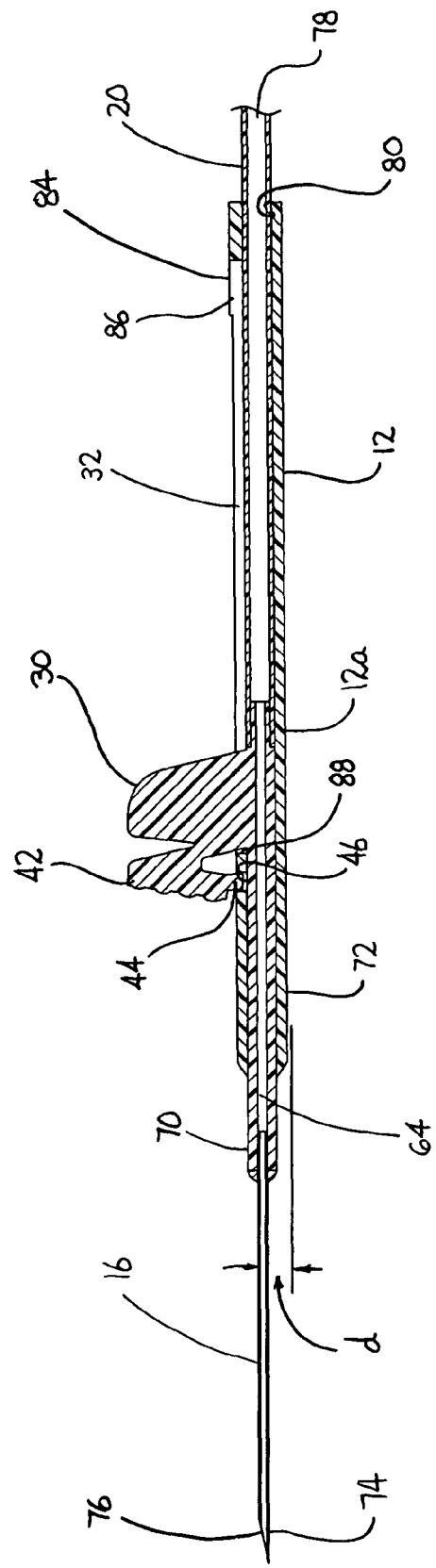
FIG. 4 is a side view, shown in section, of the embodiment of FIG. 1 with the needle in the extended position.

As noted above, during the insertion of prior art safety needles into the arm of a patient, the operator typically grasps one or both of the flexible wings of the safety needle in order to hold the safety needle and advance the needle into the arm of the patient. The flexibility of the wing or wings may make it difficult to accurately position the needle within a vein. As further noted above, safety needle 10 is provided with rigid wing structure 22 to positively stabilize safety needle 10 on the arm of a patient. In order to advance needle 16 of safety needle 10 into the arm of the patient, safety needle 10 is provided with a dorsal fin or engagement member 30 which is configured to be gripped between the thumb and first finger of the operator in order to advance needle 16 into the arm of a patient. In this particular embodiment, dorsal fin 30 is formed on or attached to hub 14 (FIG. 4). Alternately, one or both of rigid wings 28a and 28b can be grasped to advance safety needle 10 into the arm of a patient.

In order to move hub 14 to advance needle 16 from elongate housing 12 and to retract needle 16 safely within elongate housing 12, elongate housing 12 is provided with a longitudinal slot 32 extending substantially the length of elongate housing 12. Dorsal fin 30 is movable within slot 32 to facilitate movement of hub 30 within elongate housing 12. A lockout structure is associated with slot 32 in order to secure dorsal fin 30 within a proximal most position within slot 32 and prevent reuse of safety needle 10. Specifically, a pair of projections 34a and 34b extend inwardly into slot 32. Projections 34a and 34b include angled edges 36a and 36b, respectively, which are configured to engage dorsal fin 30 as dorsal fin 30 is moved proximately within slot 32. Engagement of dorsal fin 30 with angled edges 36a and 36b spreads or forces slot 32 apart to allow dorsal fin 30 to pass proximally therethrough. Once dorsal fin 30 has moved to a proximal most position within slot 32, perpendicular edges 38a and 38b, on projections 34a and 34b respectively, prevent dorsal fin 30 from being moved distally within slot 32 thereby locking hub 18 and needle 16 safely within elongate housing 32 and preventing any further reuse of safety needle 10.

Figure 2:
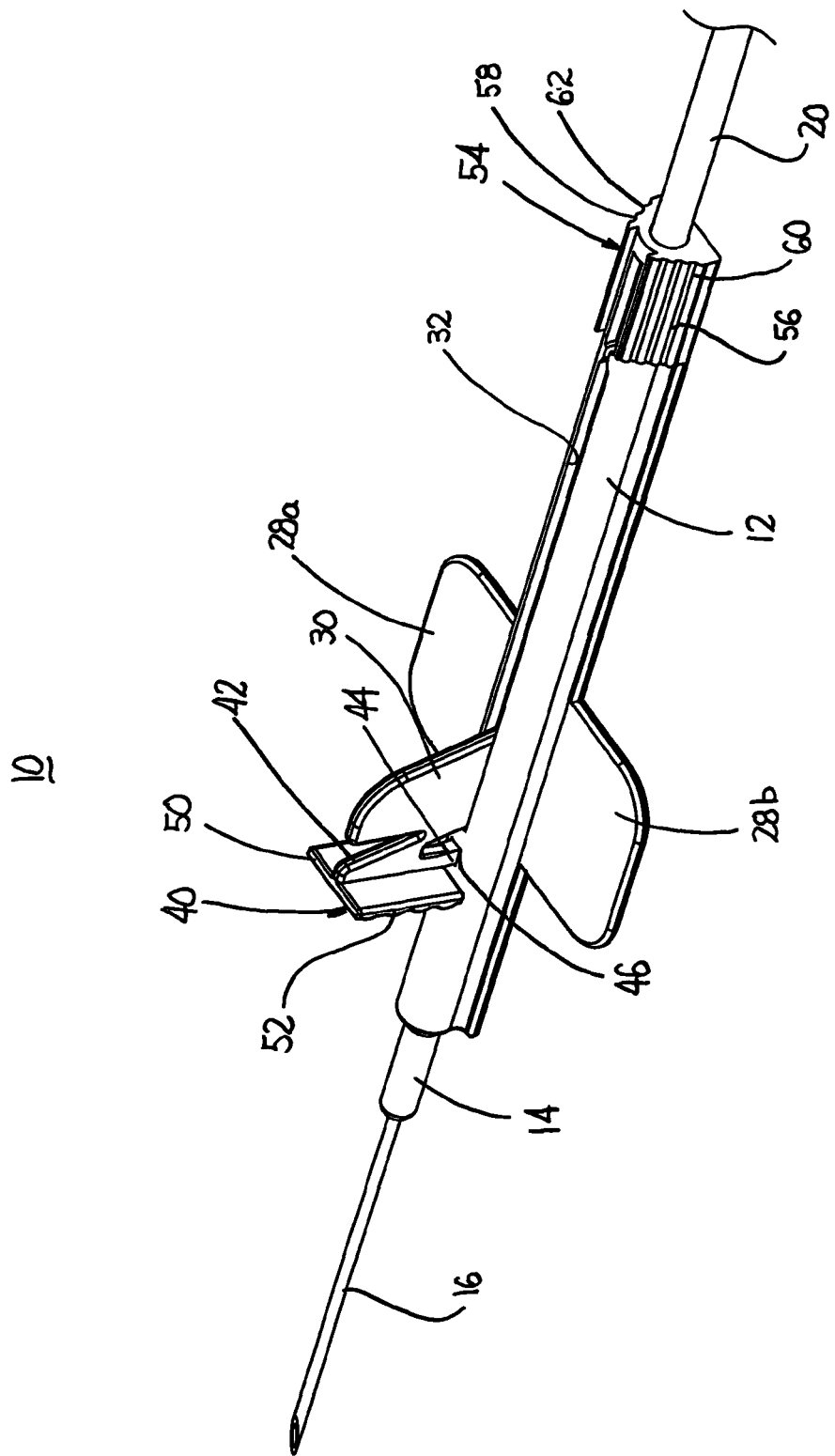
FIG. 2 is an alternative perspective view of the embodiment of FIG. 1.

Referring now to FIGS. 1 and 2, safety needle 10 further includes a release mechanism 40 which is configured to maintain hub 14 in a distal most position relative to elongate housing 12 during insertion of needle 16 into the arm of a patient. Specifically, release mechanism 40 includes a flexible finger 42 (FIG. 2) associated with hub 14 and having a projection 44 which is configured to engage a notch 46 formed in elongate housing 12 at a location distal of slot 32. Flexible finger 42 is configured to bias projection 44 into slot 32. By moving flexible finger 44 in a proximal direction, projection 44 is pivoted or moved out of engagement with notch 46. In this embodiment, flexible finger 44 it is mounted to, or formed on, dorsal fin 30. A finger pad 50 is mounted on flexible finger 44 to provide a larger surface area to effect proximal movement of flexible finger 44. A front surface 52 of finger pad 50 is ribbed to prevent the operator's finger from slipping on finger pad 50. A rear surface of finger pad 50 functions as a lockstop such that if a clinician's finger slips off dorsal fin 30 during insertion of safety needle 10 into a patient, the rear surface of pad 50 prevents movement of a clinician's finger or hand distally of pad 50. The provision of finger pad 50 on flexible finger 44 also facilitates movement of dorsal fin 30 proximally within slot 32.

Safety needle 10 is also provided with a proximal finger gripping surface 54 which facilitates insertion of safety needle 10 into the arm of a patient and, more particularly, greatly facilitates the withdrawal of needle 16 of safety needle 10 from within the arm of the patient. Specifically, with reference to FIG. 2, finger gripping surface 54 generally includes a first finger gripping surface 56 on one side of slot 32 and a second finger gripping surface 58 on the opposed side of slot 32. First finger gripping surface 56 may include a ribbed surface 60 and second finger gripping surface 58 may also include a ribbed surface 62 to prevent slipping of fingers while gripping safety needle 10.

Figure 3:
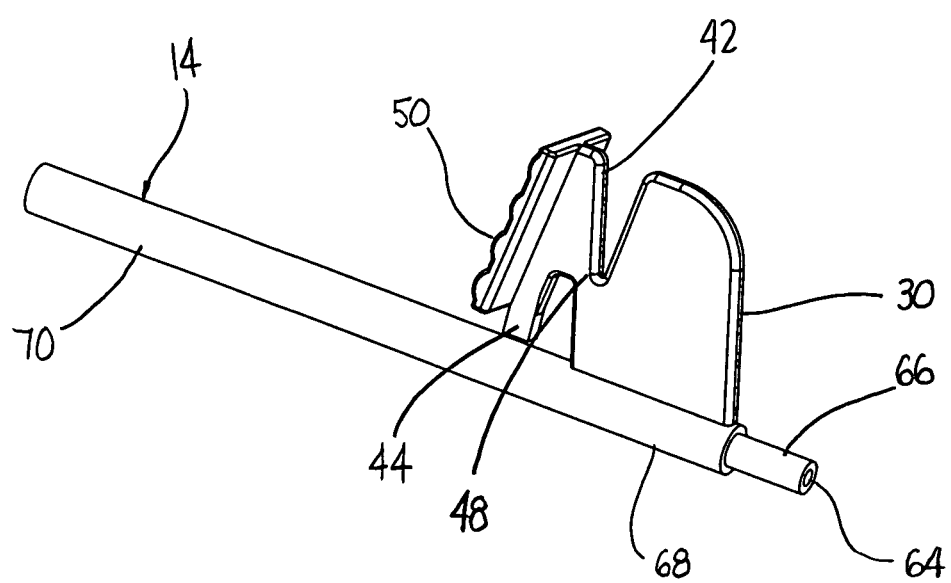
FIG. 3 is a perspective view of a hub, dorsal fin and release mechanism.

Referring now to FIG. 3, hub 14 will now be described in detail. Hub 14 includes a bore 64 which allows hollow needle 16 to be in fluid communication with tubing 20. Hub 14 includes a stepped down portion 66, adjacent a proximal end 68 of hub 14, to receive tubing 20. Hub 14 also includes a transparent zone 70 in order to visualize the flow of fluid through bore 64. This is desirable in order to ensure needle 12 is properly inserted within the vein of the patient and that the desired fluids are viewed flowing through needle 12, i.e., flashback is observed.

As noted hereinabove, in one embodiment, flexible finger 42 is mounted on dorsal fin 30 at a pivot point 48. Pivot point 48 may be integral with flexible finger 42 and fin 30 in the form of a flexible or living hinge or, alternatively, flexible finger 42 and dorsal fin 30 may be separate structures connected at pivot point 48 by known pivotal connection means. Although dorsal fin 30 is illustrated as being formed on proximal portion 68 of hub 14, dorsal fin 30 may be positioned anywhere along the length thereof.

Referring now to FIG. 4, needle 16 and hub 14, in the extended position, extend from a distal end 72 of elongate housing 12. Needle 16 includes a sharp tissue penetrating needle tip 74 and a needle bore 76 extending through needle 16. Needle bore 76 is in fluid communication with bore 64 of hub 14 and is in fluid communication with a bore 78 of tubing 20. As noted hereinabove, hub 14 along with needle 16 and tubing 20 are movably mounted within a bore 80 of elongate housing 12.

A particular advantage of the manually activated retraction mechanism of safety needle 10 is that, in the absence of a retraction spring provided within elongate housing 12, surgical needle 16 maintains a generally low-profile in relation to the arm of the patient. Specifically, the distance "d" between needle 12 and a bottom surface of rigid wing 24 is minimized. This allows insertion of needle 16 into the patient's arm at a relatively low angle of attack and allows rigid wing 24 to lay flatter against the arm of the patient thereby increasing stability of safety needle 10 as fluids are inserted or withdrawn from the arm of the patient. Additionally, the manual retraction of hub 14 and specifically needle 16 within elongate housing 12 allows the operator to control the rate of retraction of needle 16 to prevent any spilling of fluids and, more importantly, to control the position of needle 16 during the retraction of needle 16.

As also shown in FIG. 4, in the extended position, projection 44 of flexible finger 42 engages notch 46 in elongate housing 12 to maintain hub 14 in a distal most position within housing bore 80. As described hereinabove with respect to FIGS. 1 and 2, a proximal end 84 of slot 32 defines a lockout zone 86 and notch 46 is provided distally of distal end 88 of slot 32.

Figure 5:
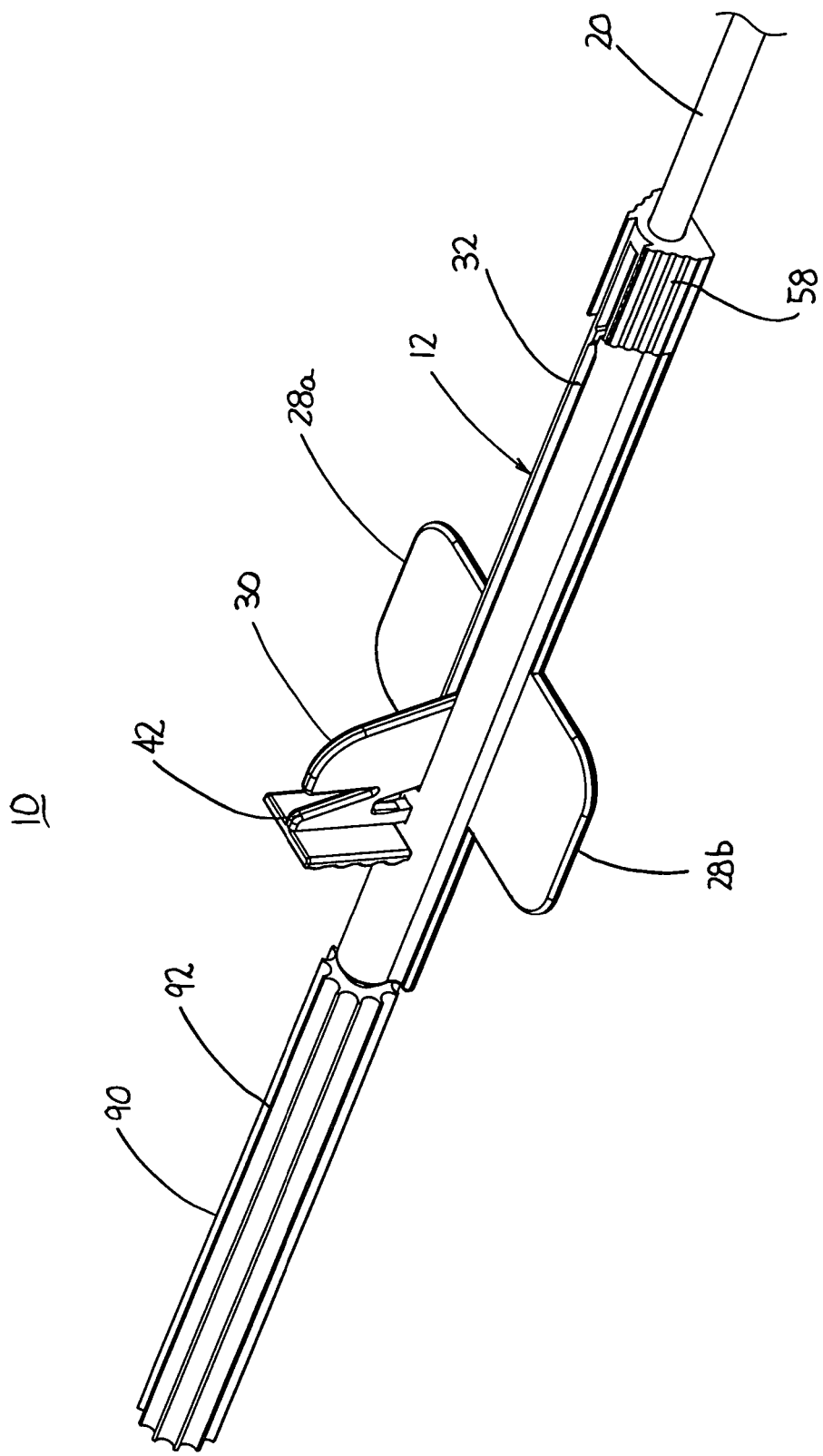
FIG. 5 is a perspective view of the embodiment of FIG. 1 with a safety sheath attached.

Referring for the moment to FIG. 5, in one embodiment, safety needle 10 includes a needle safety sheath 90 covering needle 16 to prevent needlestick injury to the user prior to use of safety needle 10. In a particular embodiment, safety sheath 90 is provided with a longitudinally ridged outer surface 92 to enhance gripping of safety sheath 90 and removal of safety sheath 90 from needle 16.

Figure 6:
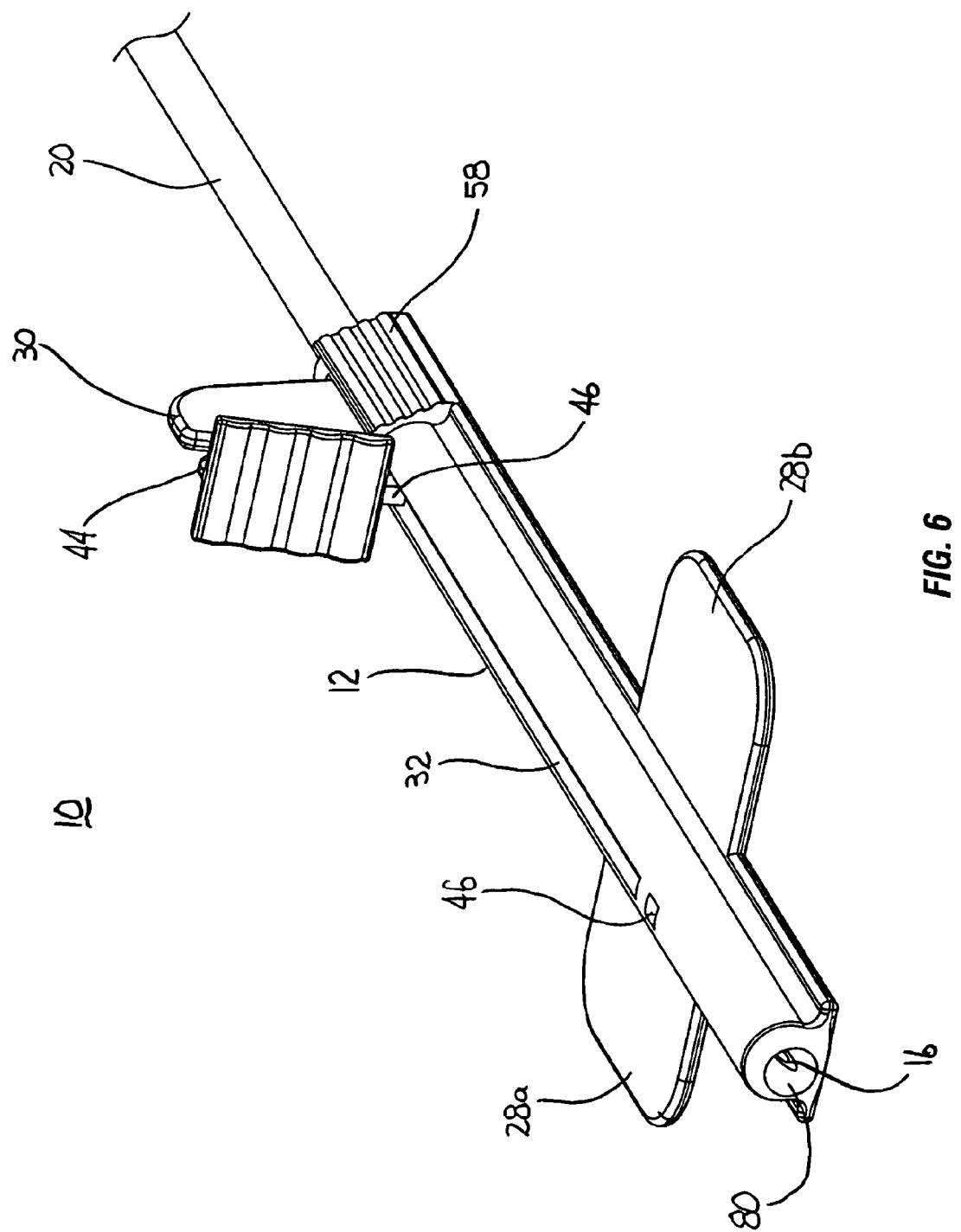
FIG. 6 is a perspective view of the embodiment of FIG. 1 with the needle in a retracted position.
Figure 7:
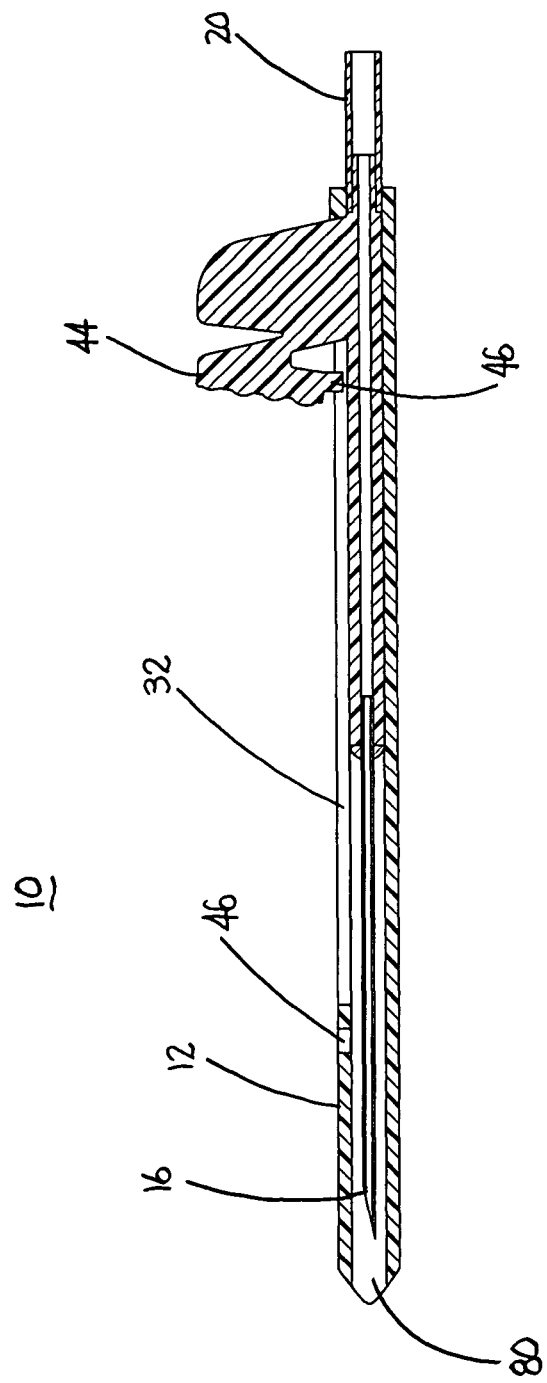
FIG. 7 is a side view, shown in section, of the embodiment of FIG. 1 in the retracted position.
Figure 8:
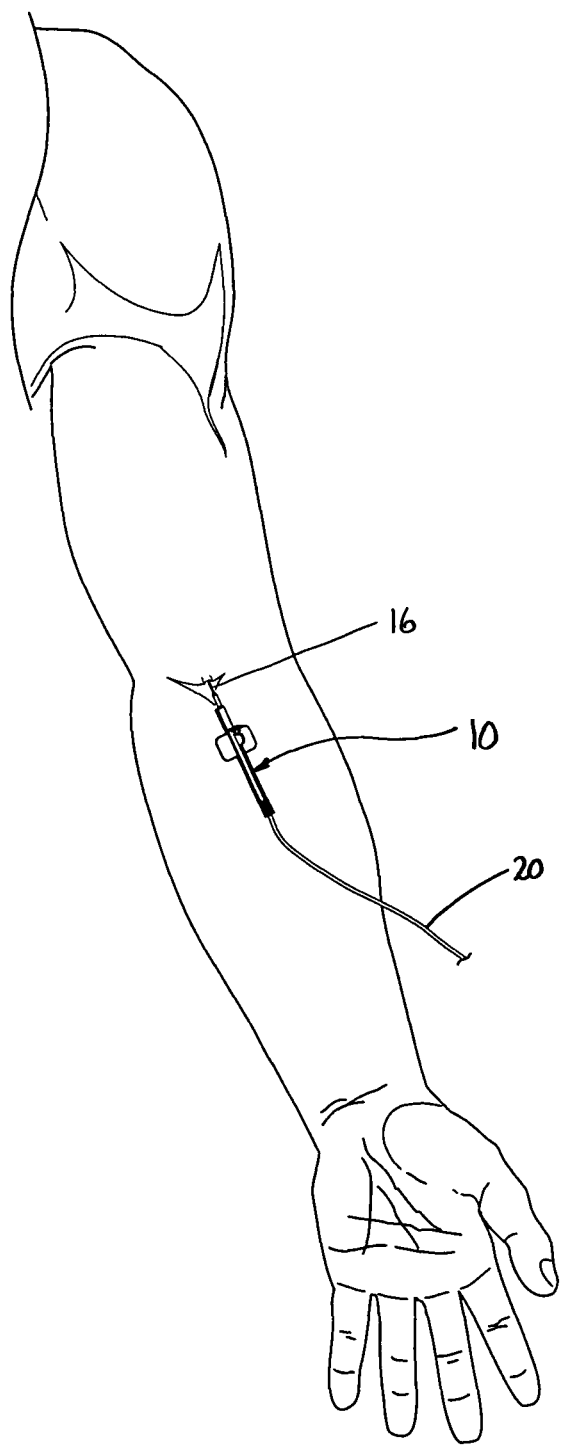
FIG. 8 is a perspective view of the embodiment of FIG. 1 inserted in a patient.

Referring now to FIGS. 4-7, in using safety needle 10 to inject or withdraw fluids from the arm of the patient, safety needle 10 is in an initially extended configuration such that needle 16 and hub 14 extends distally from elongated housing 12. Projection 44 of flexible finger 42 is engaged within notch 46 of elongate housing 12 to secure a needle 16 in the extended position (FIG. 4). As noted above, safety needle 10 is typically provided with a safety sheath 90 (FIG. 5) covering needle 16 which must be removed prior to use of safety needle 10. Once safety sheath 90 has been removed, safety needle 10 can be grasped by the user to insert needle 16 into the arm of a patient. Specifically, dorsal fin 30 is grasped between the thumb and first finger of the user to facilitate the insertion of needle 16 into the patient's arm (FIG. 8). Additionally, proximal finger gripping surface 54 may be used to assist insertion. At this point, when needle 16 has been properly inserted within the arm of a patient, fluid should be seen flowing through transparent zone 70 of hub 14.

Once the desired fluid transfer flow has been completed, proximal finger gripping surface 54, specifically first side 56 and second side 58, are grasped between the thumb and first finger of the user to draw safety needle 10 proximally and thereby remove needle 16 from the arm of the patient. Additionally, dorsal fin 30 may also be grasped to facilitate removal. In conjunction with, or subsequent to, the removal of needle 16 from the arm of the patient, flexible finger 44 may be biased proximally about pivot point 48 to draw projection 44 out of notch 46 in elongate housing 12. Further proximal pressure on flexible finger 44 will move dorsal fin 30 proximally within slot 32 thereby drawing hub 14 and needle 16 within elongate housing 12 to safely shield needle 16.

As dorsal fin 30 is moved to a proximal most position within slot 32, fin 30 engages angled edges 36a and 36b to spread apart slot 32 in the area of projections 34a and 34b to allow dorsal fin 30 to move into lockout zone 86 (FIGS. 1 and 2). Any attempt to move dorsal fin 30 distally within slot 32 will cause fin 30 to engage perpendicular edges 38a and 38b of projections 34a and 34b, respectively, thereby preventing further distal movement of dorsal fin 30. In this manner, safety needle 10 is locked out against any reuse and needle 16 is safely retained within bore 80 of elongate housing 12 (FIGS. 6 and 7).

Figure 9:
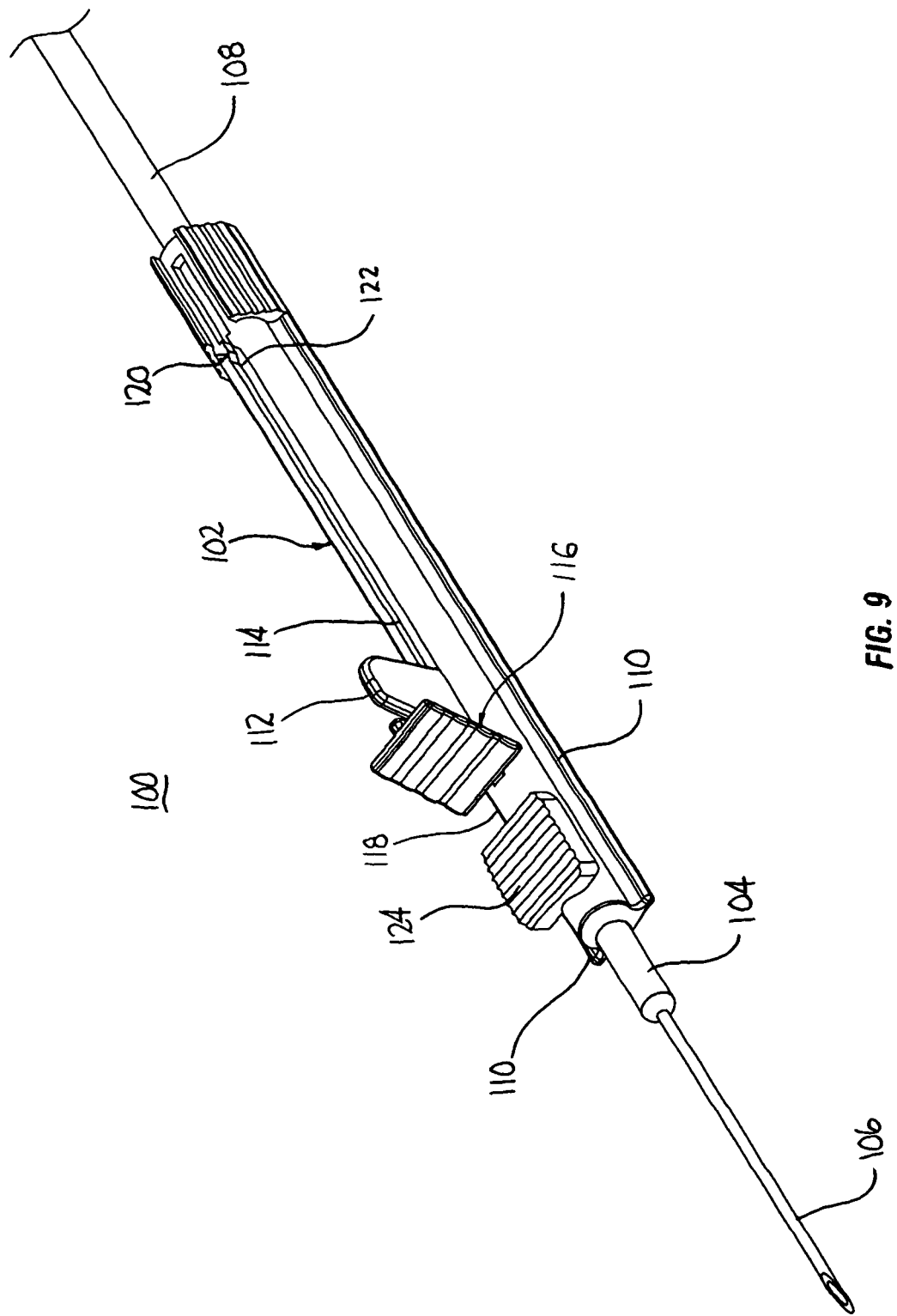
FIG. 9 is a perspective view of an alternative embodiment of a manually retracted safety needle device having a rigid wing structure.

Referring now to FIG. 9, in an alternative embodiment of the presently disclosed safety needle, shown generally as 100, the safety needle includes an elongate housing 102 and a hub 104 movably mounted within elongate housing 102. Safety needle 100 is substantially similar to safety needle 10 and includes a needle 106 extending distally from hub 104. Tubing 108 extends out of housing 102 and is in fluid communication through hub 104 with needle 106. In this embodiment, an extension 110 extends longitudinally along the length of the underside of elongate housing 102. In particular applications, the provision of perpendicular rigid wings, such as, for example, perpendicular rigid wings 28a and 28b of safety needle 10, may not be desired. In the absence of perpendicular rigid wings, the overall size of the packaging used to transport safety needle 100 can be minimized to reduce costs. Further, the attendant costs associated with the manufacture of safety needle 100 are reduced. Moreover, a configuration of narrow rigid wings permits use at areas of the body where space is limited.

Similar to safety needle 10, safety needle 100 includes a dorsal fin 112 movable longitudinally within a slot 114 formed in elongate housing 102. Safety needle 100 also includes a release mechanism 116 provided adjacent a distal end 118 of slot 114 and lockout structure 120 provided at a proximal end 122 of slot 114. Release mechanism 116 and lockout structure 120 perform substantially identically to those described hereinabove with respect to safety needle 10.

Safety needle 100 further includes a finger pad 124 which is configured to receive the thumb of the user as safety needle 100 is grasped and needle 106 is inserted into the patient. Finger pad 124 provides an additional grasping surface on safety needle 100 to facilitate manipulation of safety needle 100.

Figure 10:
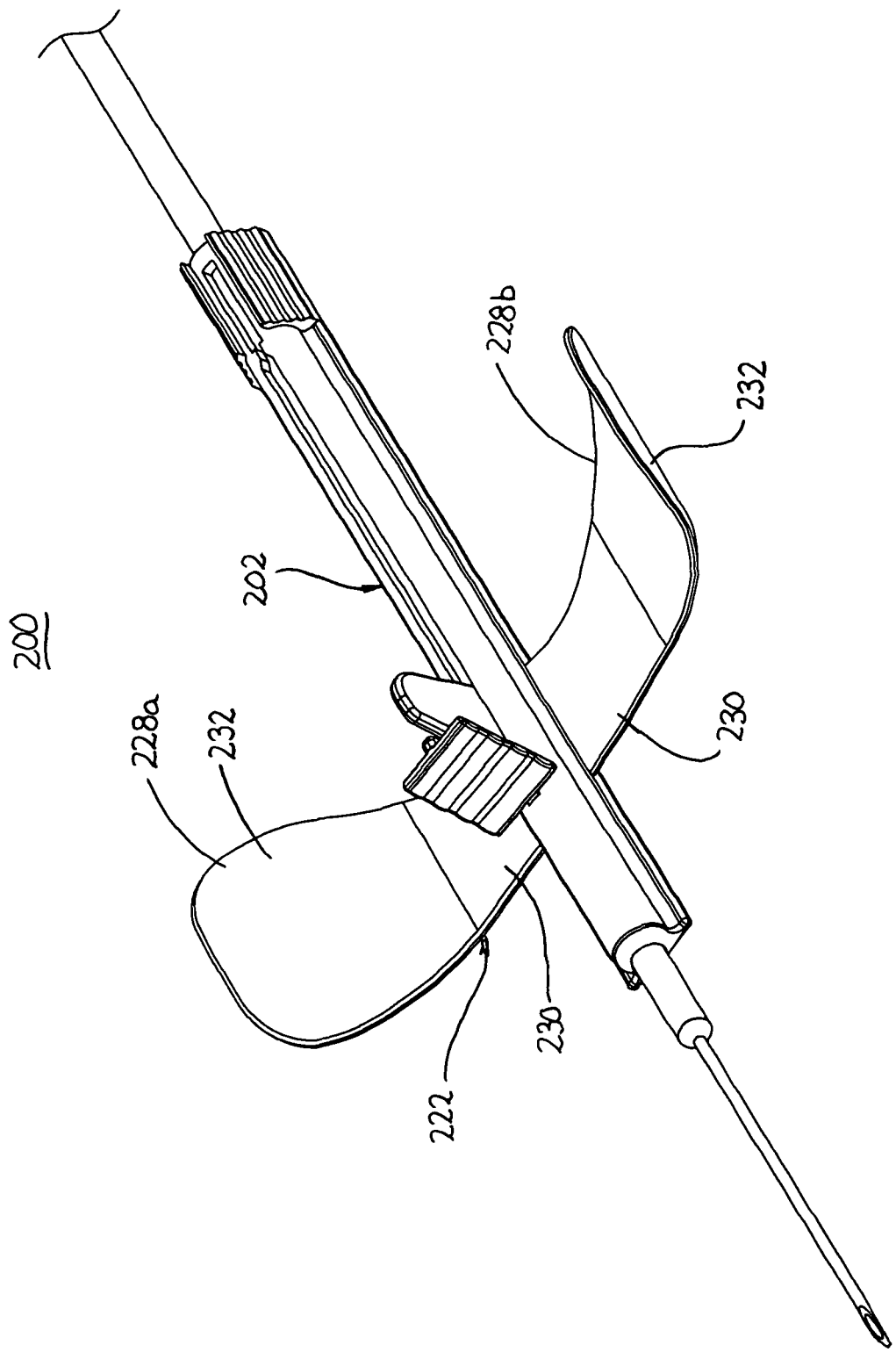
FIG. 10 is a perspective view of another embodiment of the presently disclosed manually retracted safety needle device.
Figure 11:
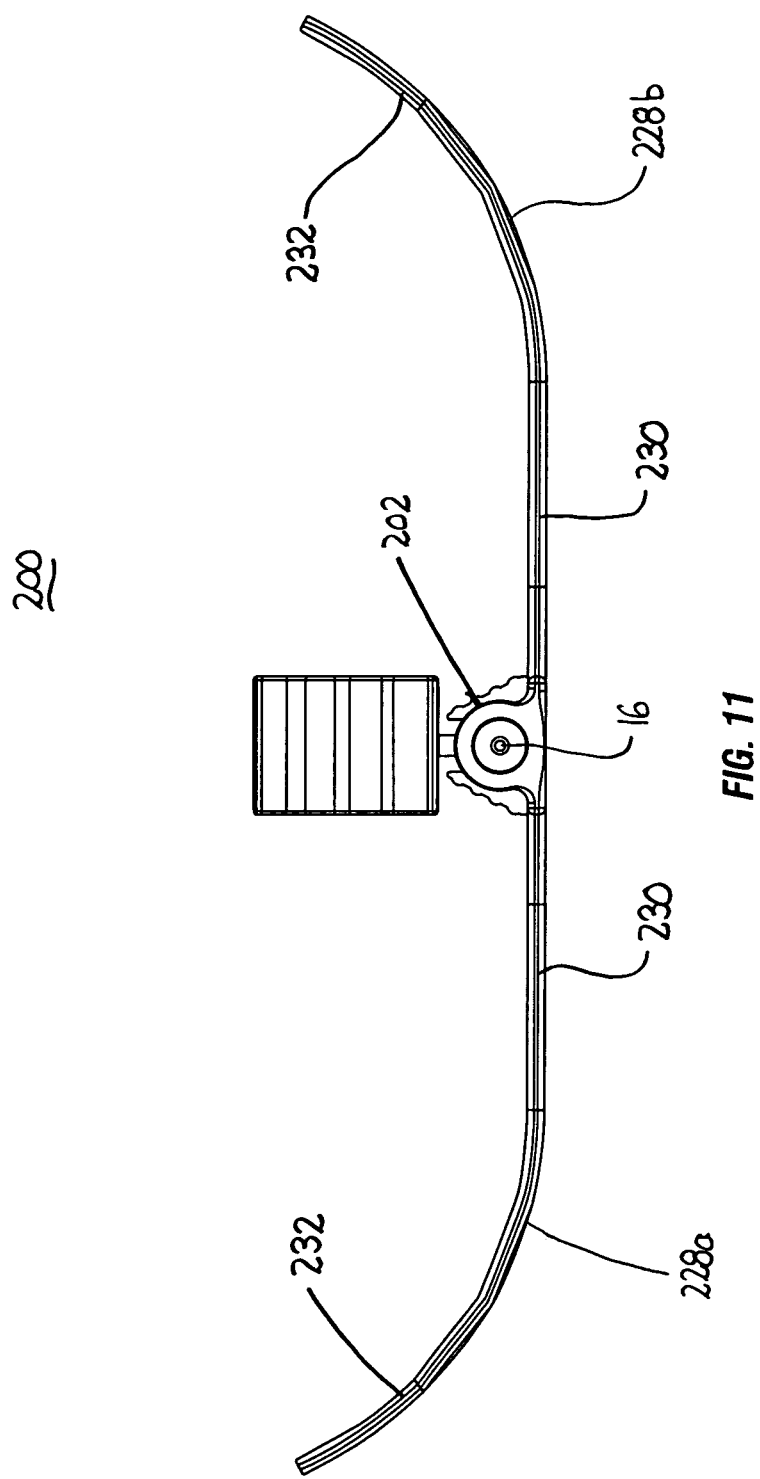
FIG. 11 is a front view of the manually retracted safety needle device shown in FIG. 10.

FIGS. 10 and 11 illustrate another embodiment of the presently disclosed safety needle shown generally as 200. Safety needle 200 is substantially the same as safety needle 10 with the exception that the at least one rigid wing structure 222 includes first and second wing halves 228a and 228b which are curved. More specifically, each of wing halves 228a and 228b includes a linear inner portion 230 extending from elongate housing 202 and a curved outer portion 232. Curved outer portion 232 and linear inner portion 230 define a recess contoured to receive the thumb of a clinician. Either or both of wing halves 228a and 228b can be grasped by a clinician or medical assistant to facilitate insertion of safety needle 210 into a patient.

Figure 12:
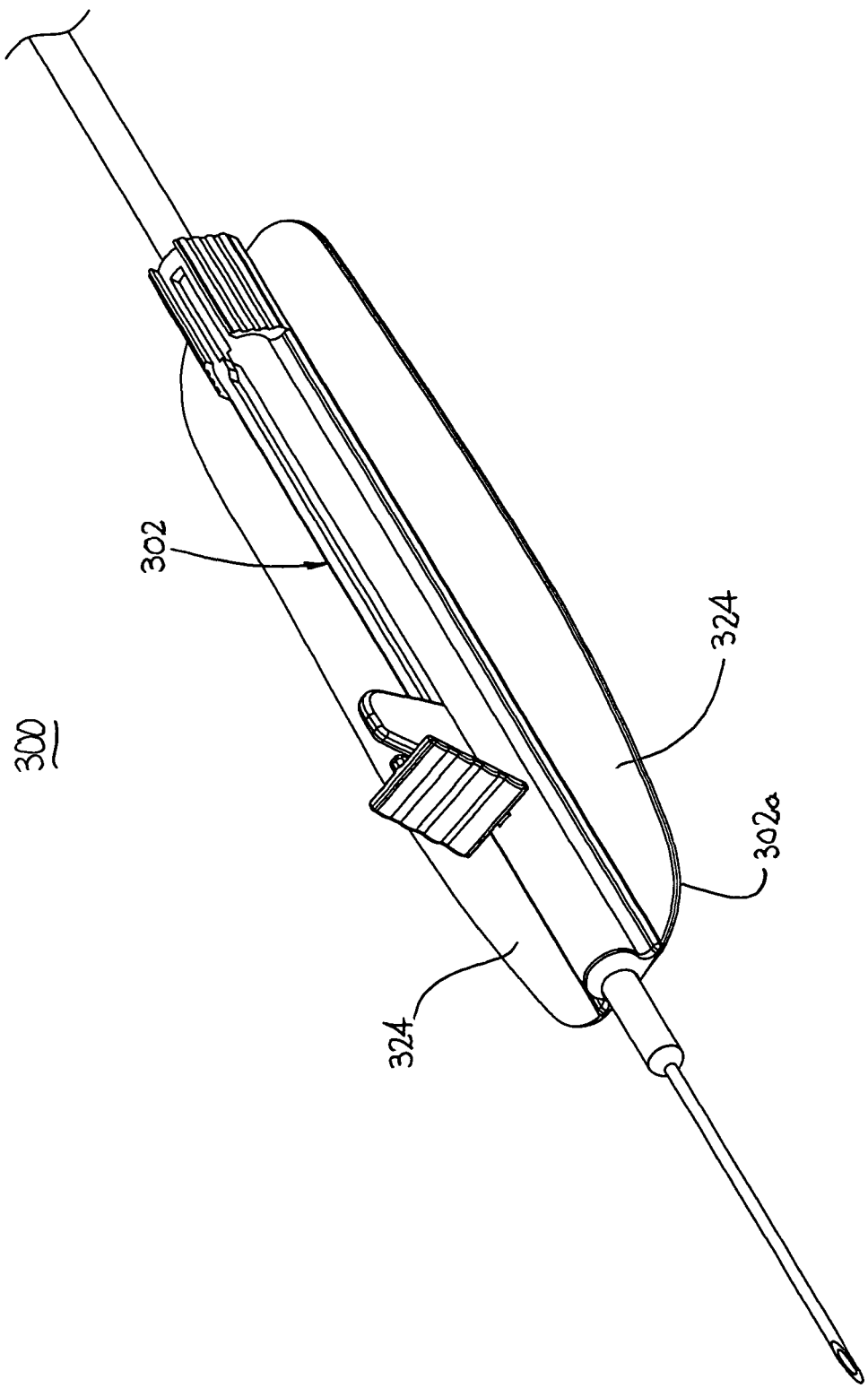
FIG. 12 is a perspective view of yet another embodiment of the presently disclosed manually retracted safety needle device.

FIG. 12 illustrates yet another embodiment of the presently disclosed safety needle shown generally as 300. Safety needle 300 is substantially the same as safety needle 10 with the exception that rigid extensions 324 extend outwardly from elongated housing 302 a substantial distance, e.g., from about ¼ to about ⅜ of an inch. Alternately, other extension dimensions are envisioned. Although extensions 324 are illustrated to extend along the entire length of housing 302, extensions 324 can extend along only a portion of the length of housing 302. As illustrated, extensions 324 and housing 302 define a flat or substantially flat support surface 302a for supporting safety needle 300 on a patient's arm.

It will be understood that various modifications may be made to the embodiments disclosed herein. For example, the disclosed dorsal fins may be provided permanently affixed to the elongate housing of the safety needle and the flexible finger can be pivotally mounted directly to an associated hub. Further, the sizes and shapes of the disclosed rigid safety wings may be varied depending upon the intended application, such as, for example use in other areas of the body such as the leg, chest etc, or preferred holding method for a device. Additionally, alternative gripping structures may be provided along the length of the elongate housing to facilitate insertion and withdrawal of the needle from the body of a patient. Therefore, the above description should not be construed as limiting, but merely as exemplifications of particular embodiments. Those skilled in the art will envision other modifications within the scope and spirit of the claims appended hereto.

The invention claimed is:

1. A safety needle device comprising:
   an elongate housing having a notch in an exterior surface and a longitudinal slot extending along the housing between a distal end and a proximal end;
   a hub movably mounted within the elongate housing;
   a hollow needle extending distally from the hub;
   a dorsal fin having a length, the dorsal fin rigidly connected to the hub along the entire length of the fin and extending outward through the slot, said needle being covered by the housing when the fin is adjacent the proximal end of the slot and exposed when the fin is adjacent the distal end of the slot; and
   a projection pivotably connected to the dorsal fin outside the housing for engaging the notch in the elongate housing when the dorsal fin is adjacent the distal end of the slot to selectively prevent movement of the hub relative to the elongate housing so the needle is exposed for use.

2. The safety needle device as recited in claim 1, further comprising a pair of wings extending outward from the exterior surface of the elongate housing.

3. The safety needle device as recited in claim 2, wherein the pair of wings extend laterally from opposite sides of the elongate housing.

4. The safety needle device as recited in claim 1, further comprising:
   a finger pivotally attached to the dorsal fin, said projection extending from the finger; and
   a pad mounted on the finger to facilitate pivoting the finger with respect to the dorsal fin, thereby pivoting the projection.

5. The safety needle device as recited in claim 1, further comprising a lockout mechanism including a lockout projection extending into the longitudinal slot adjacent a proximal end of the housing and the dorsal fin is movable proximally beyond the lockout projection to retain the fin adjacent the proximal end.

6. The safety needle device as recited in claim 5, wherein the lockout projection includes a proximal edge extending substantially perpendicular to the housing slot and a distal edge extending at an angle to the proximal edge.

7. The safety needle device as recited in claim 1, further comprising a finger gripping surface positioned at a proximal end of the housing, wherein the finger gripping surface has a ribbed portion.

8. A safety needle device comprising:
   an elongate housing having an opening in an exterior surface;
   a hub moveably mounted within the elongate housing and having a longitudinal axis;
   a needle extending distally from the hub along the longitudinal axis;
   a dorsal fin extending outward from the hub parallel to the longitudinal axis of the hub and having a length, the dorsal fin rigidly connected to the hub along the entire length of the fin;
   a projection pivotably connected to the dorsal fin outside the housing for engaging a notch in the elongate housing to selectively prevent movement of the hub relative to the elongate housing;
   a finger pad pivotally connected to the dorsal fin and positioned outside the elongate housing between the dorsal fin and the needle; and a ribbed finger gripping surface provided on a proximal end of the elongate housing including a plurality of parallel ribs extending along the housing parallel to the longitudinal axis of the hub.

9. The safety needle device as recited in claim 8, wherein the elongate housing includes a longitudinally extending slot and the finger gripping surface includes first and second portions positioned on opposite sides of the longitudinally extending slot.

10. The safety needle device as recited in claim 8, wherein the finger gripping surface extends around a portion of the periphery of the proximal end of the elongate housing.

11. The safety needle device as recited in claim 8, further comprising a lockout projection extending into the slot for engaging the dorsal fin to retain the needle in a position in which the needle is covered by the housing.

12. The safety needle device as recited in claim 11, wherein the lockout projection includes a proximal edge extending substantially perpendicular to the housing slot and a distal edge extending at an angle to the proximal edge.

13. The safety needle device as recited in claim 8, wherein the finger pad a plurality of parallel ribs extending lateral to the housing.

14. A safety needle device comprising:
a hollow elongate housing having a slot extending through a top of the housing in a longitudinal direction, the elongate housing having a flat surface;
a hub movably mounted within the elongate housing for movement between an advanced position and a retracted position, the hub having a fixed dorsal fin extending through the housing slot, the dorsal fin having a length, the dorsal fin rigidly connected to the hub along the entire length of the fin;
a needle extending distally from the hub;
a pair of wings extending from the flat surface of the elongate housing on opposite sides of the slot;
a pair of side extensions, each of the side extensions extending longitudinally along an outer surface of the elongate housing and outwardly from the flat surface of the elongate housing;
a finger pad pivotably supported by the dorsal fin of the hub, the finger pad supporting a projection positioned to engage a portion of the elongate housing to prevent the hub from moving relative to the housing, the projection disengaging from the portion of the elongate housing when the finger pad is pivoted relative to the dorsal fin to enable the hub to move relative to the elongate housing; and
a locking zone within the slot configured to engage the dorsal fin to maintain the hub in the retracted position.

15. The safety needle device as recited in claim 14, wherein the finger pad extends over both sides of the slot.

16. The safety needle device as recited in claim 14, wherein each wing extends longitudinally along an outer surface of the elongate housing.

17. The safety needle device as recited in claim 14, wherein each wing extends generally laterally from the elongate member.

18. The safety needle device as recited in claim 17, wherein each wing is generally rectangular.

19. The safety needle device as recited in claim 14, wherein at least a portion of the hub is transparent to facilitate viewing fluid flowing therethrough.

20. The safety needle device as recited in claim 14, further comprising a lockout projection extending into the slot positioned for retaining the dorsal fin in the locking zone to maintain the hub in the retracted position.

21. The safety needle device as recited in claim 20, wherein the lockout projection includes a proximal edge extending substantially perpendicular to the housing slot and a distal edge extending at an angle to the proximal edge.

22. The safety needle device as recited in claim 20, wherein the lockout projection constitutes a first lockout projection and the device further comprises a second lockout projection extending into the slot from an opposing side of the slot.

* * * * *